United States Patent
Hainfeld et al.

(10) Patent No.: US 6,818,199 B1
(45) Date of Patent: Nov. 16, 2004

(54) MEDIA AND METHODS FOR ENHANCED MEDICAL IMAGING

(76) Inventors: James F. Hainfeld, 44 Bradley Dr., Shoreham, NY (US) 11786; Daniel N. Slatkin, 2415 Long Creek Dr., Southold, NY (US) 11971

(*) Notice: Subject to any disclaimer, the term of this patent is extended or adjusted under 35 U.S.C. 154(b) by 51 days.

(21) Appl. No.: 10/093,770

(22) Filed: Mar. 8, 2002

Related U.S. Application Data

(63) Continuation-in-part of application No. 09/619,343, filed on Jul. 19, 2000, now Pat. No. 6,369,206, which is a division of application No. 09/039,601, filed on Mar. 16, 1998, now Pat. No. 6,121,425, which is a continuation-in-part of application No. 08/652,007, filed on May 23, 1996, now Pat. No. 5,728,590, which is a continuation-in-part of application No. 08/282,929, filed on Jul. 29, 1994, now Pat. No. 5,521,289.

(51) Int. Cl.[7] .......................... A61K 51/00; A61K 49/04
(52) U.S. Cl. .................... 424/1.11; 424/1.17; 424/1.45; 424/9.4
(58) Field of Search .............................. 424/179.1, 1.29, 424/1.11, 1.17, 1.45, 9.4; 530/391.1–391.9

(56) References Cited

U.S. PATENT DOCUMENTS

| | | | |
|---|---|---|---|
| 5,019,370 A | * | 5/1991 | Jay et al. ........................ 424/4 |
| 5,360,895 A | | 11/1994 | Hainfeld et al. .......... 530/391.5 |
| 5,443,813 A | | 8/1995 | Hainfeld ...................... 424/1.17 |
| 5,690,903 A | | 11/1997 | Hainfeld ...................... 424/1.49 |
| 5,707,986 A | | 1/1998 | Miller et al. ................. 514/185 |
| 5,750,150 A | | 5/1998 | Okazaki et al. .............. 424/682 |
| 6,169,917 B1 | | 1/2001 | Masotti et al. ............... 600/407 |
| 6,203,778 B1 | | 3/2001 | Brasch .................... 424/9.411 |
| 6,225,303 B1 | | 5/2001 | Miller et al. ................. 514/185 |
| 6,265,875 B1 | | 7/2001 | Saranathan et al. ......... 324/314 |

FOREIGN PATENT DOCUMENTS

JP 10-330288 12/1998

OTHER PUBLICATIONS

XP-002233810, K. Ogawara et al, Journal of Controlled Release 61 (1999), Re: "Mechanisms of hepatic disposition of polystyrene microspheres in rats: Effects of serum depend on the sizes of microspheres" article, pp. 241–250.

* cited by examiner

Primary Examiner—Hankyel T. Park
(74) Attorney, Agent, or Firm—Alix, Yale & Ristas, LLP

(57) ABSTRACT

Metal nanoparticles are described that are useful for enhancing the contrast of x-rays or other radiation sources. A method is disclosed whereby the agents are administered intravenously or intra-arterially to detect coronary senses and other vascular features. It is also disclosed how directing moieties attached to the metal particles are used to detect specific targets.

20 Claims, 2 Drawing Sheets

No Contrast Agent  Gold Nanoparticle Contrast Agent

MEDIA AND METHODS FOR ENHANCED MEDICAL IMAGING

CROSS-REFERENCE TO RELATED APPLICATIONS

This application is a continuation-in-part of U.S. patent application Ser. No. 09/619,343 filed Jul. 19, 2000 now U.S. Pat. No. 6,369,206; which is a divisional of application Ser. No. 09/039,601, filed Mar. 16, 1998 and issued as U.S. Pat. No. 6,121,425; which is a continuation-in-part of application Ser. No. 08/652,007, filed May 23, 1996 and issued as U.S. Pat. No. 5,728,590; which is a continuation-in-part of application Ser. No. 08/282,929, filed Jul. 29, 1994 and issued as U.S. Pat. No. 5,521,289.

BACKGROUND OF THE INVENTION

This invention relates generally to enhance medical imaging. More particularly, the present invention relates to metal particle agents and the methods of their use in medical imaging.

The practice of medicine was revolutionized by the discovery of x-rays by Roentgen in 1895. Today, over 300 million diagnostic x-ray examinations are performed each year in the United States. Even with the rapid growth of Magnetic Resonance Imaging (MRI), 75 to 80% of all diagnostic imaging utilize X-rays.

X-rays show bone structure well, but for better delineation of soft tissue structures, including vasculature, the alimentary canal (digestive tract), and bladder, contrast agents are required to enhance image contrast. Sodium iodide was first used in 1923 to opacify the bladder, and shortly afterwards the intravenously administered agent sodium 5-iodo-2-pyridone-N-acetate (Uroselectan) was introduced for imaging the urinary tract. Water soluble, ionic, triiodobenzene contrast agents were then developed for intra vascular use, such as diatrizoate and ioxaglate. These, however, unpredictably and occasionally caused moderate to severe anaphylactic, cardiovascular and pain reactions. Part of this toxicity was later found to be a result of the high osmolality, so agents that were non-ionic with lower osmolality were developed, such as the monomeric iohexol (also called by the trade names Omnipaque and Exypaque), based on German patent 2,726,196, corresponding to U.S. Pat. No. 4,250,113, and a dimeric version with even lower osmolality, iodixanol (trade names Accupaque and Visipaque), described in European patent 108,638.

Currently there are two types of X-ray image contrast enhancing agents approved for human use: a) aromatic iodinated compounds that are water soluble, and b) barium sulfate suspensions, used only for gastrointestinal tract imaging.

The development of the above-mentioned contrasting agents notwithstanding, several serious medical problems persist that affect millions of individuals which could be addressed using even better contrast agents. One such problem is the large number of sudden unexpected heart attacks and deaths that occur. Each year in the U.S. 1,100,000 new and recurrent heart attacks occur, resulting in 500,000 deaths per year. It is the number one killer. Heart attacks often occur suddenly without warning, when a coronary artery with plaque buildup (atherosclerosis) breaks loose, initiating a clot that blocks the artery (myocardial infarction). Heart muscle dies due to lack of oxygen, the heart pumps insufficiently, brain function is destroyed, and the victim commonly may die before adequate treatment is obtained.

Plaque buildup and narrowing of the coronary arteries occurs over a period of years, but few people know the condition of their coronary arteries and the risk and danger thereof. If the condition of the coronary arteries was known, treatments could be administered before the cataclysmic event occurred, and many sudden fatal heart attacks could be avoided. The reason that routine checks of the coronary arteries are not done with annual physicals, or for persons over a certain age or believed to be at risk is that the current best test, coronary angiography, which images the coronary arteries directly and permits visualization of constrictions, is itself an expensive, complicated, time-consuming, and risky procedure. This test involves piercing a leg or arm artery (which is under high pressure) with a needle, snaking a catheter through the arteries to the heart, and watching coronary arterial blood flow in real-time using X-ray fluoroscopy. A very concentrated iodine dye is injected, which, for a few seconds, provides sufficient contrast to allow the coronary arteries to be imaged. This procedure requires the services of a skilled cardiologist and operating team. A number of possibly fatal events could be initiated by the procedure such as blood clots in major, vital arteries (caused by the catheter dislodging pieces of plaque from the artery wall) resulting in stroke, massive reaction to the dye, cardiac arrhythmia, damage or puncture of arteries, infection, hemorrhage, and heart attack.

Coronary angiography carries with it these major complication rates—death (0.12–0.20%), cerebrovascular accident (0.03–0.20%), myocardial infarction (0.0–0.25%); and minor complication and local infection (0.57–1.6%) or arrhythmia (0.30–0.63%). Total risk of serious complications is 1.7%. About one out of every 600 persons subjected to such trans-arterial coronary angiography die from the procedure alone. Due to the high level of invasiveness and risk, it is not recommended for routine use and especially not for the elderly and those in poor health, namely those who need it most. Yet, about 1,250,000 cardiac catheterizations for coronary angiography are performed annually in the United States at a cost of $5,000 to $6,000 per procedure. The high cost of the procedure and associated risk therefore make routine coronary angiography inappropriate for use as a screening test.

The ability to perform non-invasive coronary angiography would represent a major improvement in patient care. Information regarding coronary anatomy could then be acquired with minimal risk, even for patients in whom coronary angiography is contraindicated due to severe allergic history to current radiographic contrast agents, fever with documented infection, bleeding diatheses, recent gastrointestinal bleeding, or cerebrovascular accident. Follow-up angiographic information in patients undergoing revascularization procedures could also be more readily obtained.

Echocardiography and Doppler techniques use ultrasound, and can be done in a doctor's office, with no risk. These techniques provide information about the size of the heart chambers, the pumping function, valve function, and blood volume. However, they are not suitable for anatomic evaluation of the coronary arteries Since 1973, Computed Tomography (CT) has grown to become one of the most important radiological examination processes in the industrialized world. CT delineates organs in a new way by producing digitally reconstructed images of cross-sections of a patient. In this way, it achieves a higher than normal sensitivity to improve the natural radiological contrasts between organs. It is exceptionally sensitive to contrast media, moreover, and can detect disease-related abnormalities from the distribution of an intravenous dose of a contrast medium.

Consequently, 60–80% of all CT examinations involve the use of a contrast medium. The primary uses for CT include brain and spine investigations, abdominal and urological studies, and approximately 20% of all CT procedures are performed to investigate the liver. An advanced CT technique, called spiral or helical CT, has been developed which achieves the resolution of normal CT but with shorter examination times and a lower x-ray dose. Multi-slice CT (MSCT) is another improvement, with typically 2 or 4 source/detector pairs operating simultaneously, which can improve the resolution and acquisition time.

Electron Beam Computed Tomography (EBCT), or Ultrafast CT, uses a rapid x-ray scanner, which can freeze the heart beating motion, to visualize calcification in the coronary arteries without use of dyes or catheterization.

Electron Beam Tomography (EBT) scanner is different from conventional (mechanical) CT scanners, focusing an electron beam onto tungsten target rings positioned around the patient. Each sweep of the electron beam produces a continuous 30 degree fan beam of x-rays that pass through the patient to a stationary array of detectors which generates cross-sectional images, with scan times of 50 milliseconds. Exposures can be triggered from an electrocardiogram (ECG or EKG) to visualize a specific part of the beating heart cycle and to reduce overall dose.

Intra vascular ultrasound (IVUS) is an invasive technique, where the sound equipment is on the catheter snaked into the artery. This technique allows the architecture of the wall, its components, size, shape, surface and consistency to be analyzed.

Stress echo combines treadmill exercise with an ultrasound echocardiogram and EKG to measure differences between resting and active states. A low-resolution image is created by moving a transducer over the chest area. This gives some information about heart output and overall function, but is not suitable for anatomic evaluation of the coronary arteries.

In nuclear perfusion studies, single photon emission tomography (SPECT), radioactive isotopes are injected into the patient and detectors yield a low-resolution map of the heart. This test reveals perfusion abnormalities, but does not depict the coronary artery stenosis that cause them nor does it provide direct measurements of coronary artery blood flow. It is not suitable for anatomic evaluation of the coronary arteries.

Positron-emission tomography (PET) utilizes positron emitting radioactive isotopes which are injected into the patient and detectors which yield a low resolution map of the heart. This test also reveals perfusion abnormalities, but due to the limited resolution is not able to show the coronary artery constrictions that cause them nor does it provide direct measurements of coronary artery blood flow. It is not suitable for anatomic evaluation of the coronary arteries.

Some studies have shown sensitivity and specificity for coronary artery disease for Magnetic Resonance Angiography (MRA) to be as high as 80–90%, but others have not found the method to be as accurate. Problems include limited spatial resolution, mis-registration of images acquired over sequential breath holds, and inadequate flow contrast. This last problem might be ameliorated by the use of improved contrast agents. However, resolution is significantly worse than with x-ray angiography, making constrictions more difficult to definitively detect. Further development is required before coronary MRI becomes a standard clinical tool.

Even though each of these alternative technologies has some usefulness in assessing coronary function, all of them fall short of providing the best direct, necessary, and sufficient images needed for life-saving decisions which are possible with contrast-based x-ray angiography. Coronary angiography remains the standard for assessment of anatomic coronary disease, because no other currently available test can accurately define the extent of coronary luminal obstruction. However, because the technique can only provide information about abnormalities that narrow the lumen, it is limited in its ability to accurately define the etiology of the obstruction or detect the presence of non-obstructive atherosclerotic disease. Despite these and other limitations, coronary angiography is the only method currently available for defining the details of the entire coronary endoluminal vascular anatomy, and it provides the reference standard against which other tests are compared. Information derived from such angiograms is the standard by which mechanical interventions and many medical therapies are planned. In addition, prognostic information is also gained from data regarding coronary artery patency.

The Hounsfield Unit (HU) is a measure of the relative density of a structure on Computed Tomography (CT), named after the inventor of CT, Sir Geoffrey Hounsfield. It is used to measure the amount of x-ray attenuation of each voxel in the image; since the voxel is normally represented as a 12-bit number, the scale ranges from −1024 to +3071. By definition, water has a HU of zero. Air is −1024 HU, fat is −50 to −100, muscle is 40, soft tissue is 30–80, calcification is 80–1000, bone is 800–1000, and metal is 2000. The reading in HU is also called the CT number. The addition of about 42 $\mu$g iodine/ml increases the contrast by one HU.

Virtually all possible elements and known compounds have been explored to some extent to find improved x-ray contrast agents. In *Metal-Based X-ray Contrast Media*, Yu, S. B. and Watson, A. D., Chem.

Rev., vol. 99, pp. 2353–2377, 1999, the authors conclude that "[f]rom the list of possible heavy metals, we may exclude those metals that are radioactive (Th, U), those that are highly toxic . . . (Hg, Pb, Tl, Cd, Ag) or those that are unduly expensive (Pt, Ir, Os, Au, Pd) from consideration. Furthermore, those elements close to iodine (In-Ba) do not offer any advantages over iodine in terms of their ability to utilize high-energy x-ray photons (thus lowering the radiation exposure to patients) and can also be eliminated. This leaves only the lanthanide metals and Hf, Ta, W, Re, and Bi as potential candidates." Unfortunately, no viable candidates have been produced. "The challenge to move to an entirely new technology platform and successfully develop an adequate first-generation metal-based compound which could compete with the current generation of iodinated materials is immense and in our minds presently remains unsolved."

SUMMARY OF THE INVENTION

Briefly stated, the invention in a preferred form is a medical imaging method and contrast agent which contrasts a targeted portion of a body of a living animal. The method includes intravenously administering a quantity of nanoparticles sufficient to contrast the targeted portion of the body under irradiation and irradiating the targeted portion of the body with penetrating radiation. Each of the nanoparticles has a metallic core surrounded by a surface layer including a component having an affinity for the targeted portion of the body.

The targeted portion of the body is irradiated a predetermined period of time after the nanoparticles are administered, such that an optimum combination of targeted portion nanoparticle concentration and targeted portion to background nanopartiacle distribution is achieved.

The metal nanoparticles have a core composed of gold, platinum, palladium, thallium, bismuth, osmium, iridium, silver, tungsten, lead, tantalum, or uranium. The component of the material of the surface layer may be for example, an antibody, an antibody fragment, a peptide, a lipid, a carbohydrate, a nucleic acid, or a drug. The surface layer may also include a component that absorbs X-rays. Either the surface layer or the metallic core may include a radioactive isotope.

In one preferred method, where the targeted portion of the body is cancerous cells, the component of the material of the surface layer is an antibody, an antibody fragment, or a peptide.

In another preferred method, where the targeted portion of the body is a blood clot, the component of the material of the surface layer is anti-fibrin, anti-D-dimer antibodies, or peptides.

If the targeted portion of the body is an atherosclerotic plaque, the component of the material of the surface layer may be either DMP-444 or a lipophilic group.

The location and extent of an infection site may also be determined by extracting blood from the animal, isolating leukocytes or white blood cells from the extracted blood, and labeling the isolated leukocytes or white blood cells with nanoparticles. Nanoparticles of this type are attracted to an infection site.

It is the object of the invention to provide improved medical imaging methods and contrast agents.

It is also an object of the invention to provide medical imaging methods and contrast agents for targeting selective regions of the body.

It is further an object of the invention to provide medical imaging methods and contrast agents for detecting blood vessel abnormalities in the heart, carotid arteries, brain, kidney, extremities, intestine, and other soft tissues.

It is still further an object of the invention to provide medical imaging methods and contrast agents for detecting functional states of tissues.

BRIEF DESCRIPTION OF THE DRAWINGS

The present invention may be better understood and its numerous objects and advantages will become apparent to those skilled in the art by reference to the accompanying drawings in which.

DETAILED DESCRIPTION OF THE PREFERRED EMBODIMENT

Figures 1A, 1B:
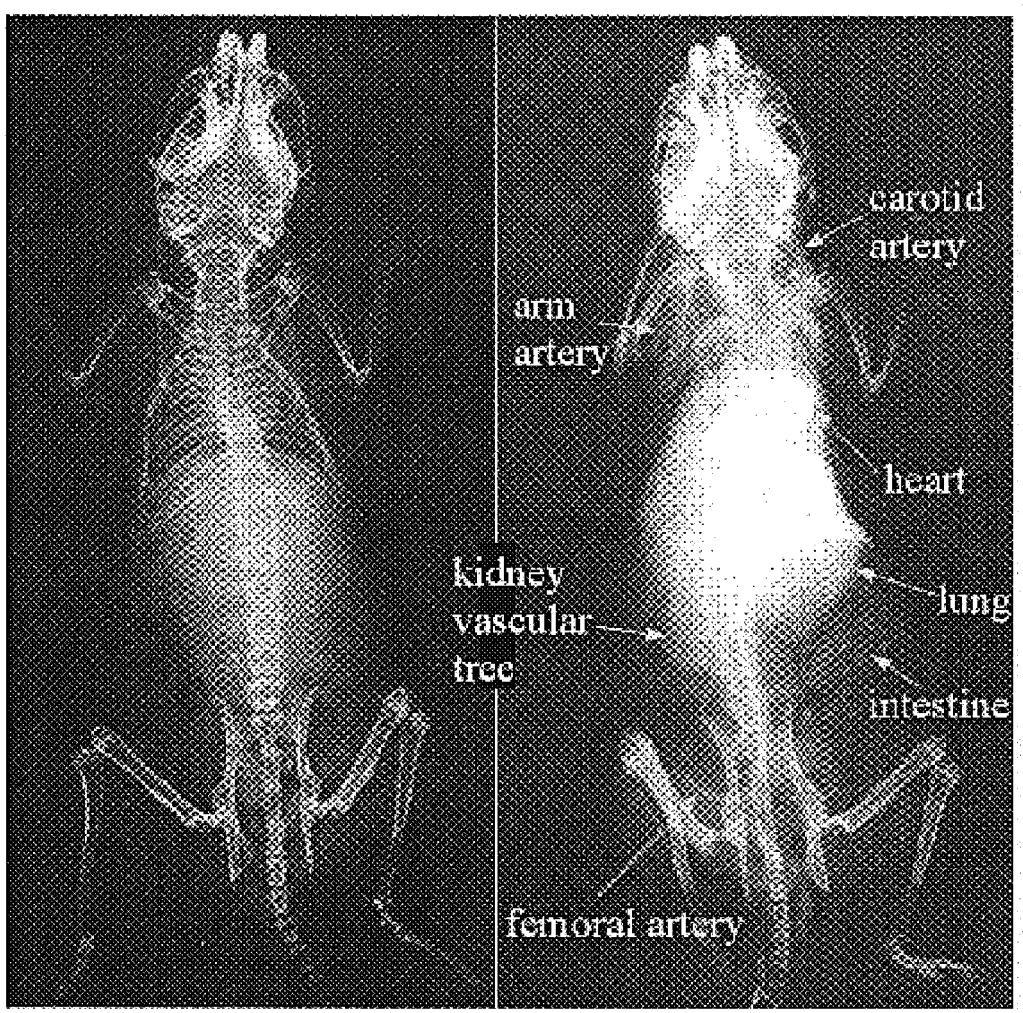
FIGS. 1a and 1b are X-ray images of Balb/C mice taken without a contrast agent and with a gold nanoparticle contrast agent in accordance with the invention, respectively.
Figure 2A:
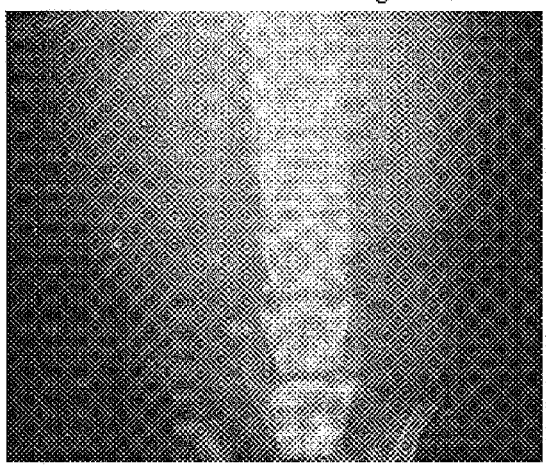
FIGS. 2a and 2b are enlarged X-ray images of the abdominal areas of the mice of FIGS. 1a and 1b, respectively, illustrating the kidney vascular trees and intestinal arteries disclosed by the gold nanoparticle contrast agent.
Figure 2B:
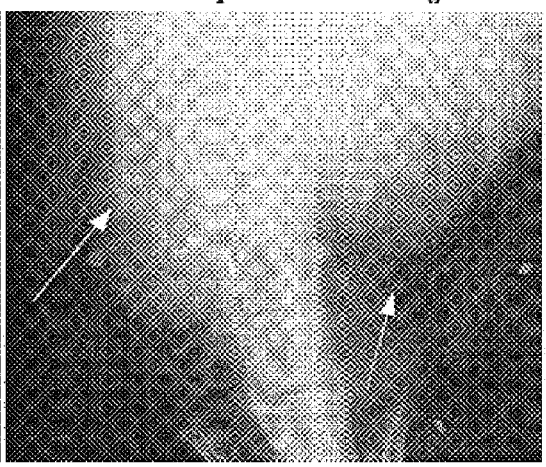

Successful contrast agents must fulfill a number of criteria. They must be non-toxic, clear the body in a reasonable time, provide sufficient contrast for image enhancement, and be non-immunogenic. Osmolality must be low to prevent osmotic imbalance and undesirable physiological responses. Pain after administration should be minimal or absent. The standard vascular agents for x-ray imaging are based on iodine compounds, and most contain tri-iodinated benzene ring structures. Although these are commonly used, they show some toxicity, can be painful after injection, and can be immunogenic. The present invention utilizes gold nanoparticles that fulfill the above-listed criteria for imaging agents better than conventional agents and without the side effects produced by conventional agents.

One such preferred gold compound synthesized and found to be useful is a gold nanoparticle with a gold core approximately 2 nm in diameter, which contains about 240 gold atoms. "Metal particle" or "metal nanoparticle" are defined to be all constructs having a metal core ranging from 0.5 to 500 nm in size. "Gold particle" or "gold nanoparticle" are defined to be all constructs having a gold core ranging from 0.5 to 500 nm in size. Larger or smaller gold compounds, clusters, particles and colloids may also be utilized. For example, gold may be formed into $Au_6$ clusters, undecagold clusters ($Au_{11}$), $Au_{55}$, $Au_{67}$, $Au_{75}$, and gold colloids that are typically characterized by their gold diameter (from 0.5 nm to 100 nm).

The number of gold atoms per particle or size of the particle can are related by the simple formula for the volume of a sphere, $V=4/3 \times \Pi \times r^3$, where V is the volume of the particle and r is its radius. For the density of gold of 19.3 g/cc, this formula then becomes, $$n = 315 \times p \times d^3 / A$$

where n is the number of atoms, p is the density in g/cc, d is the diameter in nm, and A is the atomic mass. For gold, this reduces to:

$$n = 30.9 \times d^3$$

The calculated number of gold atoms in particles of various sizes is provided in Table 1, below:

TABLE 1

| Diameter (nm) | Number of Gold Atoms |
|---|---|
| 1.4 | 85 |
| 2 | 247 |
| 3 | 834 |
| 5 | 3,863 |
| 10 | 30,900 |
| 15 | 104,288 |
| 20 | 247,200 |
| 40 | 1,977,600 |
| 100 | 30,900,000 |

An important performance issue in imaging is to the contrast obtainable with various elements and compounds, just based on their physical x-ray absorptive properties. Most diagnostic x-ray imaging machines operate in the 25 to 150 keV range. In this range, absorption, and therefore contrast, is dominated by the photoelectric effect, which is proportional to $Z^3$, where Z is the atomic number. The Z of iodine is 53, whereas the Z of gold is 79, giving an advantage of $(79/53)^3 = 3.31$ for a gold atom compared to an iodine atom. If one considers the advantage on a weight basis, gold has an atomic weight of 197, whereas iodine is 127, so for the same weights, iodine would have $197/127 = 1.55$ more atoms. The overall advantage of gold vs. iodine on a weight basis is then $3.31/1.55 = 2.14$. This means the contrast will be approximately double for a gold agent compared to one containing an equal weight of iodine. More detailed analysis, however, shown below, indicates that the gold can be a factor of three or more better than iodine on a weight basis.

The design of the gold nanoparticle imparts several important properties to the agent, which distinguish it from, and enhance it over, current agents. Gold is very dense and has a high atomic number, so that it highly absorbs x-rays. The gold core has a density of about 19.3 g/cm$^3$. By contrast, Iodixanol, the commonly used angiographic contrast agent, has a density of about 0.68 g/cm$^3$, and contains 6 iodine atoms. On a molecule to molecule basis (where a "molecule" in the gold case is taken to be a single gold particle), the gold construct will absorb far more of the x-ray beam. For example, at 100 keV photon energy, each gold atom is about 3 times more absorbent of the x-ray beam than iodine, and each molecule of gold, for a 2 nm particle contains 247/6=41 times as many atoms than a molecule of iodixanol. Therefore, per molecule, the gold will be about 3×41=123 times more effective as a contrast agent.

In addition to the enhanced contrast obtained by using higher atomic number elements, the contrast also, from physical principles and measurements, varies with and is better at optimal photon energies. Several factors are important for choosing the optimal x-ray voltage and photon energy. The x-ray absorption of elements and soft tissue generally decreases with increasing photon energy. However, at the elemental electronic binding energies, the absorption increases, or jumps, often by a factor of four or so, for example at the K, L, and M shell orbital electronic binding energies. Since the absorption is increased above such energies, one would expect better contrast just above these energies. Contrast may be roughly estimated from the known absorptions of the element divided by the absorption of soft tissue, as given in Table 2, where the X-ray absorption and contrast of iodine and gold are Compared at various photon energies (iodine K edge is at 33.2 keV and gold K edge is at 80.7 keV).

synchrotron, where two or more images are collected at and around the K edge of the element of interest. Post processing of this data can sensitively detect the element and additionally, the dose to the patient can be reduced. The metal particles of this invention are well suited to this type of detection.

One serious side effect of the current iodine agents has been found to be due to their high osmolality (the osmolality of a solution is a measure of the number of dissolved particles per kilogram of water). High osmoiality contrast media tend to have more adverse effects associated with discomfort arising from intra-arterial injection than contrast media with a low osmolality. In the range of concentrations required for good X-ray visualization, the high osmolality of most agents relative to blood plasma and surrounding tissues causes leaching of water across semipermeable membranes, resulting in undesirable physiological effects.

Current aqueous solutions of iodine agents that are sold may contain iodine concentrations of 240 to 350 mg I/ml and over. For iodixanol that contains 6 iodine atoms per molecule, and is a non-ionic dimer, a 350 mg I/ml solution has an osmolality of 350/(126.9×6)=0.46 M, which is quite high. This is the best for the current iodine contrast agents. Omnipaque (iohexol), a monomeric non-ionic agent, which is widely used, only has 3 iodine atoms per molecule, so the same concentration of use would result in an osmolality of 0.92 M. By contrast, the 2 nm gold particle of this invention would at the same concentration of 350 mg Au/ml would have an osmolality of only 350/(197×247)=0.0072 M. Use of larger gold particles would result in even lower osmolalities. The present invention therefore essentially overcomes this shortcoming of current contrast agents.

TABLE 2

| Photon Energy | $\mu/\rho$ = mass attenuation coefficient cm$^2$/g | | | contrast = $(\mu/\rho_{\text{iodine or gold}})/(\mu/\rho_{\text{soft tissue}})$ | | contrast$_I$/contrast$_{Au}$ | contrast$_{Au}$/contrast$_I$ |
|---|---|---|---|---|---|---|---|
| keV | $\mu_{\text{iodine}}$ | $\mu_{\text{Gold}}$ | $\mu_{\text{soft tissue}}$ | I | Au | I advantage (>1) | Au advantage (>1) |
| 10.0 | 140.0 | 103.0 | 5.0 | 28.0 | 20.6 | 1.4 | 0.7 |
| 20.0 | 20.8 | 78.0 | 0.8 | 27.0 | 101.3 | 0.3 | 3.8 |
| 33.1 | 7.0 | 22.0 | 0.4 | 18.9 | 59.5 | 0.3 | 3.1 |
| 33.3 | 34.0 | 22.0 | 0.4 | 91.9 | 59.5 | 1.5 | 0.6 |
| 50.0 | 10.0 | 7.0 | 0.4 | 27.8 | 19.4 | 1.4 | 0.7 |
| 80.6 | 2.8 | 2.0 | 0.2 | 14.0 | 10.0 | 1.4 | 0.7 |
| 80.8 | 2.8 | 7.3 | 0.2 | 14.0 | 36.5 | 0.4 | 2.6 |
| 100.0 | 2.0 | 6.0 | 0.2 | 10.0 | 30.0 | 0.3 | 3.0 |
| 200.0 | 0.4 | 0.9 | 0.1 | 2.6 | 6.6 | 0.4 | 2.6 |
| 300.0 | 0.2 | 0.4 | 0.1 | 1.5 | 3.3 | 0.5 | 2.2 |

The data in Table 2 indicates that the highest contrast (iodine or gold absorption divided by soft tissue absorption) would be achieved just above the iodine K edge (at about 33.3 keV), and that iodine would, at that energy, produce 1.5 times the contrast of an equal weight of gold. Unfortunately, the penetration of 33 keV photons into the whole human body is poor, and consequently, many clinical x-ray machines, operate in the 100 keV range. In this region, gold has a significant advantage, and would give about three times the contrast of iodine on a weight basis. Better contrast with gold would not only improve imaging, but for the same quality image produced with iodine, use of gold would permit 3 times lower x-ray dose to the patient. This is highly significant.

K edge imaging is a powerful technique for enhancing the specific detection of a particular element. It is best used with reasonably monochromatic photon sources, such as from a Experiments have surprisingly shown that gold nanoparticles, 0.5–3 nm in size, coated with thioglucose are highly tolerated to high concentrations in vivo. Experimentally, it was shown that a blood concentration at least up to 30 mg gold/ml was tolerated in mice, with a transient weight loss observed over the next day for blood concentrations of approximately 30 mg gold/ml. This weight loss reversed itself back to normal conditions without further intervention or complication and was not observed at lower doses. 30 mg gold/ml means that 3% of the blood by weight is gold. Similar sized gold particles coated with glutathione were much less well tolerated. This is a surprising result since glutathione and glucose are both common body chemicals and are highly tolerated.

Experiments have also shown that gold nanoparticles coated with thiophenol, thio-decaborane, and mercaptoacetic acid were poorly tolerated. Hydrogen tetrachloroaurate, neutralized with base to physiological pH, where single gold atoms were in a salt form and the gold was not in nanoparticles, were found to be highly toxic and lethal. Many of these results could not be predicted or foreseen since is not entirely understood how the complex living body responds to novel chemicals or drugs. Generally, the body's response must be found empirically.

It is possible to make suitable similar contrast agents using metals other than or in addition to gold. Although gold is relatively non-toxic and non-reactive, the use of other metals could be considered for various reasons including cost, stability, or other factors. It is expected that coating other metal core nanoparticles, including ones of platinum (Z=78), palladium (Z=46), thallium (Z=81), bismuth (Z=83), osmium (Z=76), iridium (Z=77), silver (Z=47), tungsten (Z=74), lead (Z=82), tantalum (Z=73), uranium (Z=92), and others, will provide tolerance results which are similar to the use of gold (Z=79), since the bioreactivity of the organic shell and size of the nanoparticle are the major, if not the sole determinants of in vivo tolerance.

The general design of the subject nanoparticle metal contrast agents comprises a metal core surrounded by a surface layer of another material. The size of the core can be varied substantially, from 0.5 to 500 nm. This design makes tailoring such particles possible, expanding the range of properties that can be achieved. As discussed above, the metal core can consist of gold, silver, iron, platinum, palladium, iridium, tungsten, or other metals. In addition, the core can be a mixture or an ordered, concentric layering of such metals, or a combination of mixtures and layers of such metals.

For example, the metal core may be composed of two or more concentric shells of different metals. These are produced by forming the central metal particle, then plating on it an additional layer of a different metal. Non-metal elements or compounds may also be utilized for the core or one or more shells to produce a final particle with the desired properties. These particles may then be finally coated with organic molecules, forming a surface layer which may optionally include a directing moiety or more than one directing moiety for specific targeting, such as an antibody, antibody fragment, peptide, lipid, carbohydrate, nucleic acid, drug, or other molecule. One advantage of this construction as an in vivo contrast agent is that an advantageous metal that is toxic, for example the high atomic number elements lead or bismuth, may be used since they can be overcoated with an inert metal, such as gold. A further advantage is that the cost of the agent may be reduced by using a less expensive but comparably radio-opaque filler such as lead.

The surface layer is a material that is either covalently bound to the core or adsorbed and held by non-covalent forces, such as van der Waals attraction, charge, or hydrophobic interactions. Examples of covalent coupling to surface gold atoms are gold-phosphorus, gold-sulfur, and gold-amine bonds. Examples of non-covalent bonding are adsorption of proteins and polymers. The surface layer, or shell, can also be a mixture of two or more components.

As discussed above, the outer surface shell of material may include a directing moiety or more than one directing moiety for specific targeting, such as an antibody, antibody fragment, peptide, lipid, carbohydrate, nucleic acid, drug, or other molecule. In addition, it is possible to couple further components to the shell material. By such means, the directing moieties such as antibodies or peptides may be attached. They may be directly coupled to the core by attachment through a sulfur atom, for example; alternatively they may be covalently coupled to the organic shell; additionally, they may be adsorbed non-covalently to the particle or particle shell.

The shell material or directing moiety may operationally be attached by several procedures. In a first method, the material may be present during synthesis of the particle, or used in the synthesis. One example of this is the formation of single gold-phosphine compounds before a reduction step that coalesces the gold atoms into a core of multiple gold atoms. Experiments have shown that gold nanoparticles with a thiol shell can also be formed by first forming the single gold-organothiol compound, then performing a reduction step to form the multi-gold atom core with the organothiols bound to its surface. An organothiol is an organic compound containing a thiol group. In a second method, the multi-atom gold (or metal) core is first formed by reduction of a gold salt or acid. The shell compound is then added, reacting with and binding to the gold particle surface, or attaching by adsorption. In a third method, the metal nanoparticle is formed with one type of shell. An additional coating molecule of interest is then introduced, and exchanges with or replaces one of the existing coating molecules. In a fourth method, the metal core is formed with an organic shell by one of the previous methods discussed above and then additional molecule(s) are attached to the first coating.

Specific methods of producing nanoparticles which may be used as contrast agents in accordance with the subject invention are disclosed in U.S. patent application Ser. No. 09/619,343 filed Jul. 19, 2000, U.S. Pat. Nos. 6,121,425, 5,728,590, and 5,521,289, all of which have been assigned to the assignee of the subject application, and all of which are hereby incorporated by reference.

Taken together, the extremely flexible design of the metal nanoparticle permits the properties of the particles to be varied to suit the application. For in vivo use, for example, it is desirable to ensure that the particle, or at least its potentially bioreactive outer shell be non-toxic and does not bind to or accumulate in certain tissues or organs. By controlling the size of the particle and its coating or shell, we have found this to be possible.

Although various high atomic number elements have been considered for imaging, gold has been largely ignored due to its cost and the lack of suitable non-toxic compounds with appropriate imaging properties. This invention has overcome these obstacles by discovering non-toxic gold compounds and particles with suitable imaging properties that permit enhanced imaging at affordable cost.

There are several serious problems and limitations in current medical imaging which are overcome by this invention. For medical angiography, one limitation is the necessity of administering the current contrast agents intra-arterially, thus leading to risks and complications, such as thrombus formation, artery puncture, stroke, heart failure and death. A second problem is that the contrast agent itself has some toxicity, and in some individuals this may lead to anaphylactic shock, death, or kidney damage and failure. By reducing the toxicity of the contrast agent and endowing it with higher contrast per molecule, this invention makes it possible to administer such an agent by simple venous injection, and still enable adequate contrast enhancement of coronary and carotid arteries and senses if present, as well as visualization of other vascularization such as in the kidney, abdomen, limbs, brain, and in tumors. The subject contrast agents and procedures therefore overcome both limitations of current contrast agents for high-resolution imaging. They not only enable intravenous administration and subsequent clear visualization of contrasted vasculature or other structures, they also provide a lower toxicity agent and an alternative to using iodinated agents during transarterial catheterization. This is of great importance, since during an interventional procedure such as balloon angioplasty, arterial catheterization is required, and use of a lower toxicity contrast agent would reduce the risk of complications to the patient.

A third limitation is that most current imaging agents are just passive "dyes", and they cannot be targeted to specific sites. For example, iodixanol is a simple substance and does not selectively accumulate on any target tissue to enable its visualization. The agents of this invention overcome this limitation by permitting a directing moiety to be optionally attached to the nanoparticle (in their outer shell, either covalently or by adsorption), so that the agent may selectively accumulate on and contrast the target tissue. The "directing moiety" is defined as a molecule, compound or material that imparts the property of targeting or binding to specific location or tissue type. Directing moieties include antibodies, peptides, carbohydrates, lipids, drugs, nucleic acids, synthetic and natural compounds, or polymers.

Conventional contrast agents do not allow small tumors to be easily seen. In addition, conventional contrast agents and conventional medical imaging techniques generally do not distinguish between malignant and benign growths. Consequently, effective cancer diagnosis still remains elusive and often requires invasive biopsy procedures. The earlier tumors are detected, the better the prognosis generally is. In one example, breast cancer detection largely relies on noticing a "lump", but at this stage the cancer is reasonably advanced. Routine mammography has been useful to detect cancers at an earlier stage, but with this method, the radiodensity difference between the tumor and surrounding tumor is slight, since they are both soft tissue. In another example, random needle biopsies are generally taken from the prostate to detect prostate tumors. This procedure can miss the tumor completely and recurrences are not easily detected.

Intravenously injected nanoparticles having a directing moiety with an affinity for cancerous cells, such as antibodies or peptides, attached to the core will cause such a contrast agent to concentrate at the site of a tumor but not at the site of a benign growth. Tumor locations could be clearly seen and mapped, resulting in better management of the cancer. Functional imaging may also be performed, since different tissue states can be distinguished. For example, whether a tumor is benign or malignant may be detected, and tumor typing can be done to classify the tumor so that a decision of which drug it will best respond to could be made. Targeted contrast agents may be also be used to distinguish unstable atherosclerotic plaques that are at high risk of rupturing and causing a heart attack or stroke from those that are stable. Targeted nanoparticle contrast agents thereby allow a substantially non-invasive procedure at relatively low intravenous dose levels.

The agents of this invention enable targeted and functional imaging, whereas this was not previously possible with the iodine agents currently available. A fundamental reason for this is that iodine contrast molecules contain either 3 (monomer, e.g., Iohexol), or 6 (dimer, e.g., Iodixanol) iodine atoms per molecule. For example, if such a molecule is attached to a targeting antibody, and there are $10^5$ binding sites per target cell, then if 10% of these had the antibody-Iodixanol bound, this would produce an approximate iodine concentration in tissue of $1 \times 10^{-7}$ g I/cc. This would lead to an increase in contrast of only 0.002 Hounsfield Units (HU), which is not currently detectable with X-ray equipment.

This calculation may be addressed in another way, namely the delivery by antibodies of a material to a tumor. For intravenous injection of antibody conjugates, such as antibody-radioisotopes, tumor uptake may be 10–40% id/g (injected dose per gram) in mice. If each antibody had one iodixanol molecule attached (containing 6 iodine atoms), and 10 mg of antibody were injected, an uptake of 20% id/g would lead to a tumor concentration of $1 \times 10^{-5}$ g I/cc, or 0.02 HU change in contrast. This is still a challenging level to detect. However, using a 40 nm gold particle containing 2,000,000 gold atoms bound per antibody, this would instead lead to a contrast change of 6,700 HU, which greatly exceeds the defined maximum HU number.

Another example of targeting of the contrast agents disclosed is the localization of blood clots. Here the targeting moiety attached to the metal nanoparticle can be anti-fibrin or anti-D-dimer antibodies, or various peptides that have been shown to bind to fibrin.

Another example of targeted contrast agents of the present invention includes the imaging or detection of sites of infection in the body by extracting blood from a patient, isolating the leukocytes or white blood cells, labeling them with metal nanoparticles, and reinjecting them back into the patient. X-ray imaging will then reveal sites of infection since the white blood cells are attracted to and accumulate there. Although a current similar test exists using radioactive indium-111 labeled leukocytes, the metal nanoparticle approach described avoids the use of radioactivity, and its concomitant hazards of handling and disposal.

Bone scans are frequently done using Technetium Diphosphonaten (TDP), where radioactive technetium-99m is complexed with diphosphonaten. Again, the hazards of radioactivity may be avoided by using the present disclosure where the metal nanoparticles are linked to diphosphonaten or other bone-seeking agents. It is here disclosed that diethylenetriaminepentaacetate (DTPA) and other chelators may be attached to the metal nanoparticle shell which is then used to chelate tin ions which then avidly accumulate specifically on bone; this procedure will target the metal nanoparticles to bone.

The subject agents can be used to visualize plaque physiology non-invasively, and to distinguish stable from unstable plaque. Biodistribution of radioisotope-labeled antibodies have been studied extensively in vivo, especially for radioimmunotherapy. For "good" antibodies, it is not uncommon to see 20–40% id/g with a muscle uptake of about 1% id/g. If a gold-labeled agent attained 10% id/g localization in a plaque (a conservative amount compared to the above), and 15 mg was injected, the plaque would contain a gold concentration of 1.5 mg Au/cc. This would lead to a contrast of about 100 HU which is a detectable amount.

P-selectin, VCAM-1, and ICAM-1 have been shown to be expressed by endothelial cells overlying risky atherosclerotic lesions. These are some of the most important adhesion molecules implicated to date in monocyte recruitment to atherosclerotic lesions. Antibodies to these adhesion molecules (e.g., anti-P-selectin) may be attached to the metal particles for detection of these plaques.

Binding of fibrinogen to GPIIb-IIIa on agonist-stimulated platelets results in platelet aggregation, presumably by crosslinking adjacent activated platelets. Atherslerotic plaques that are at risk and thrombi contain both fibrin and platelets. Detection of activated platelets involved in thrombus formation may provide distinction between stable and unstable plaques. A peptide that has been used in vivo to identify such plaques in dogs using Tc-99 m and scintigraphy is DMP-444, which binds to the GP IIb-IIIa receptor on activated platelets. As an example, this peptide may be coupled to metal particles for high resolution functional mapping of atherosclerotic lesions.

Colored lipophilic dyes target unstable plaques, which have high lipid content. Unfortunately, these dyes are visible only in test animals that are killed and opened for examination. However, lipophilic gold particles can be prepared that have fatty acids, phospholipids, cholesterol, or other lipophilic groups on their surface. These can be used to target and delineate high-risk atherosclerotic plaques, and the gold content can be imaged by x-rays in the living patient.

For in vivo use, it is important to control the blood residence time for various uses. For renal function, rapid passage through the kidneys is desirable. This may be achieved by using a relatively small particle, about 0.5 to 3 nm. For coronary artery operations, it may be desirable to visualize the arteries for 30 minutes or more. This may be achieved by using a larger particle size to retard urinary excretion. However, very large particles (10 to 500 nm) may be efficiently removed by the reticuloendothelial system in the liver and spleen, leading to rapid blood clearance. An alternative solution to this problem is to couple the metal nanoparticle to a stable blood material, such as human serum albumin, IgG, or red blood cells. This then enhances vascular residence times to hours or days.

Experimentally, it has been found that the bodily clearance of some of the metal nanoparticle contrast agents to be exceedingly rapid. Specifically, smaller clusters, 0.5–2.0 nm (which when concentrated had a dark brown/black color) resulted in skin, eye, and extremity coloration after intravenous injection, with this coloration dissipating to approximately one-half after about 15 min. Concomitantly, the urine was dark brown/black, indicating rapid clearance of the agent through the kidneys.

The size of the nanoparticle may also be used for targeting. As described above, large particles (10 to 500 nm) are actively and efficiently removed from the blood by the reticuloendothelial system, macrophages engulf large particles by phagocytosis, and the kidneys filter and pass proteins below about 50 kDa. In addition, experimentation has shown that the kidneys pass very small nanoparticles efficiently, especially below 3 nm and preferably 0.5 to 3 nm. Thus by controlling the size of the nanoparticle from between 0.5 and 500 nm, the imageable agent nanoparticle may be directed to various tissues and organs. In another example, the neovasculature of tumors is "leaky" and some of the contrast agents developed can "leak out" or flow through the endothelium to pool at a tumor, thus marking it with high contrast. In this manner, specific targeting may be achieved without an antibody or peptide or compound that has affinity for the desired location.

In current fluoroscopy, iodine dye is injected intra-arterially, and for a few seconds the coronary arteries are contrasted, and senses may be visualized. Although trans-arterial injection is a risky procedure, dintravenous injection of conventional contrast agents would create too many problems to be considered as a viable alternative. Intravenous injection would fill the whole heart with contrast agent, as well as the lungs and other tissues, thus masking visibility of the coronary arteries. The amount of contrast agent that is administered must be greatly increased to account for the dilution which will occur before it reaches the heart.

A typical trans-arterial dose of iodinated material is about 50 g of iodine formulated as a 300 mg of l/ml aqueous solution, with about 170 ml being injected. Since the human blood volume is approximately 5 liters, it would be necessary to inject 1500 g of iodine intravenously to achieve the same contrast. If this were given in 500 ml, the injected concentration would be 3 g l/ml. For lodixanol, iodine is only 49.1% of the compound weight, so 3054 g would have to be injected at 6.1 g/ml. This is far above this compound's solubility and toxicity would be increased significantly. If it is assumed that lodixano has a solubility of 0.3 g/ml, 10.2 liters of solution would have to be injected to provide the required amount of iodine. This amount is twice the blood volume of an adult (5 liters), which is clearly impractical.

Coronary vascular imaging after intravenous iodine injection has been achieved with an injection of 160 ml of 300 mg iodine/ml (about 48 g iodine) (Achenbach S, Giesler T, Ropers D, Ulzheimer S, Derlien H, Schulte C, Wenkel E, Moshage W, Bautz W, Daniel W G, Kalender W A, Baum U. *Detection of coronary artery senses by contrast-enhanced, retrospectively electrocardiographically-gated, multislice spiral computed tomography*. Circulation. 2001 May 29;103 (21):2535–8.). Although this demonstrated an advance in iodine agent coronary artery imaging by intravenously administered iodine, more than twenty percent of the serious senses were missed by this method. Positive and certain identification was made only by using the standard trans-arterial administered contrast agent procedure. Using this case as a guideline, the final blood concentration would have been about 9.6 mg l/ml, corresponding to 228 HU. The subject gold nanoparticle contrast agent permits use of three times less gold than iodine, or 16 g of gold (final blood concentration of 3.2 mg Au/ml) due to its higher X-ray absorption. Astonishingly, it has been discovered that the gold nanoparticles of this invention have a solubility of greater than 1 g gold/ml. Consequently, the injection volume of the gold nanoparticle contrast agent could be as little as 16 ml. While this level of iodine injection led to unacceptable diagnostic results, the amount of iodine injected was close to the maximum tolerated. However, the gold nanoparticles described herein are tolerated at a minimum of 30 mg gold/ml in the blood, thus permitting the contrast to be increased approximately 10 times greater (by injecting 160 ml of 1 g Au/ml, or 160 g of gold), corresponding to 2000 HU. Similarly, an intravenous injection of 500 ml of solution (having 1 g Au/ml) will clearly provide sufficient contrast for medical imaging. While such injections are well within the realm of possibility, the solution may be diluted within reasonable limits. For example, an injection of 100 ml of 0.01 g Au/ml will provide the same blood concentration of gold as an injection of 1 ml of 1 g Au/ml.

Lower volume doses may be used for targeted nanoparticle contrast agents. Antibody localization can be 20–40% injected dose/gram (id/g), i.e., 20–40% of the amount injected is at the target site per gram of target site tissue (e.g., in a mouse). Assuming 30% id/g, and an injected amount of 1 g of gold, this would give 0.3 grams of gold/gram of tumor. This compares to a non-targeted value, where if 1 g gold was injected into the 1.5 ml blood volume of a mouse, for example, and the tumor vascular volume is assumed to be 5% of the tumor volume, leading to a concentration in the tumor of 0.033 g gold/gram of tumor. The targeted method therefore achieves a concentration factor of 9.0 (in this example).

At first glance, it would appear that nine times less gold would have to be injected to achieve the same contrast in the target. However, since the surrounding regions are not targeted, the signal-to-noise will be greatly improved for detection, and the amount of agent administered can be reduced much further. Typical antibody localizations can achieve a tumor to non-tumor ratio of 30 or more. This means that background can practically be ignored, and only enough targeted contrast agent need be injected to achieve a detectable level. An +100 HU increase in contrast is more than adequate for detection. As discussed previously, this corresponds to a gold concentration of 1.4 mg Au/ml. For a 30% id/g localization, this would then require an injection of only 4.67 mg of gold, an incredibly small amount. Since the gold particles are soluble to at least 1 g Au/ml, this would correspond to an injection volume of 0.00467 ml. Since these levels of injection are far below the tolerated amounts, this means that smaller tumors or other targets can be detected with increased doses and that the contrast can even be increased many times to visualize lower affinity targets and smaller details.

Even beyond such difficulties, if an intravenous injection of dye was possible, the x-ray machines and algorithms using computed tomography (CT) to 3-dimensionally reconstruct the heart and its vessels currently fall short of achieving comparable detection of coronary senses provided by trans-arterial angiography. CT machines have improved to collect a single exposure in 30 msec, thus providing reasonably effective stop motion. However, to see the heart in three dimensions and trace the coronary arteries, more than just one planar image is required. These may be obtained by rotating the x-ray source in a circular or spiral fashion around the patient, to acquire data from different angles. In order to avoid heartbeat motion during this series of exposures, data collection is gated using the ECG (electrocardiogram). The left main and left anterior descending arteries may be detected, but the accuracy is greatly impaired for the left circumflex and right coronary arteries due to motion. The end of diastole is often used for ECG triggering because it was believed to be the quietest time in the cardiac cycle. However, at this time the atria are contracting, thus blurring the circumflex and right coronary arteries since they lie in the atrioventricular groove. Even if triggering were improved, the vessels may not exactly return to their exact position after each beat, thus degrading the resolution of the reconstructed data.

To reconstruct the heart to high enough resolution, the number of views to be collected must be calculated. A simple formula used in reconstruction to estimate the views required for a certain resolution is:

$$n=(2d/r)^3/(2d/r)^2$$

where n is the number of views, d is the size of the object (assuming it is a cube), and r is the resolution. For the human heart, the volume of interest may be approximated as a cubical region 60 mm on a side. For a desired resolution of 0.3 mm, the number of views required is:

$$n=(2\times60/0.3)^3/(2\times60/0.3)^2=400$$

Unfortunately, even with ECG gating, the vessels are not completely reproducible in position over this time, and the reconstruction becomes somewhat blurred at the desired resolution. Thus substantial difficulties with both the dyes and instrumentation have been encountered to achieving intravenous dye administered coronary angiography.

The subject contrast agents provide higher contrast than the iodine contrast agents. Consequently, each image collected has a higher signal-to-noise and is of better quality. Therefore, the X-ray data can be collected in a shorter period of time, thereby stopping motion better. In addition, the higher quality images can be better cross-correlated so that even if there is motion from one image to another, the image structures may be correlated from image to image. Improved simple translational alignment of the images will also be possible and more sophisticated correlations are possible to correct for rotations or local distortions. In addition, nanoparticle size and/or outer coatings may be selected which will prolong the longer residence time, or blood half life of the subject contrast agents, thereby permitting collection of uniform signal data over a longer period to be reconstructed into the 3-D image. A longer residence time will also allow collection of additional data which may be used to average-out any noise which may be inherent in the particular X-ray equipment which is used.

In a preferred embodiment for coronary angiography, a contrast agent comprising gold nanoparticles having a core metal diameter of 1 to 2 nm and an outer shell of thioglucose is intravenously administered to a blood concentration of about 1 to 20 mg Au/ml. This dose level was experimentally found to be well tolerated in mice and is more than enough to produce excellent contrast with resolution of vessels at least as small as 100 microns. Senses of coronary vessels can then be clearly distinguished. This contrast agent substantially clears the blood in several hours, exiting largely through the kidneys. The contrast agent and procedure therefore fulfill the requirements for coronary angiography and overcome many of the drawbacks of the iodine-based agents, such as toxicity, high osmolality, too short a blood half-life, and failure as an intravenous agent. Since gold detection is about three times better than iodine with x-rays, the dose to the patient can be reduced. This contrast agent and procedure may also be used to assay heart function by accurately delineating blood volumes in the heart chambers.

The contrast agents may also be used trans-arterially in place of the iodine contrast agents thereby avoiding the problems associated with the iodine contrast agents, such as anaphylactic shock. Trans-arterial injection is appropriate when an angioplasty or some other catheterization procedure is required. Since the catheter is already in place, it is better and simpler to administer the contrast agent trans-arterially.

A highly related area to coronary angiography is cerebral arteriography, which is used in the diagnosis of brain circulation for stroke victims or persons at risk for brain damage. Checking on the condition and patency of the carotid arteries could prevent some strokes. Visualization of intra-cranial aneurism is also possible.

A blockage of a brain blood vessel is the most frequent cause of stroke and is responsible for about 75 percent of the nearly 150,000 U.S. stroke deaths each year. Stroke ranks as the third leading killer in the United States after heart disease and cancer. There are 500,000 to 600,000 new strokes in the United States each year. As many as 3 million Americans have survived a stroke with more than 2 million of them sustaining some permanent disability. The carotid artery is the main artery to the brain and atherosclerotic plaque there is frequently the cause of strokes. Carotid angiography is similar to coronary angiography, where a catheter is inserted into the leg or arm artery and snaked up to the carotid artery where an iodine dye is released to visualize narrowings or blockages.

The risks of current carotid angiography for diagnosing stroke are also similar to those from coronary angiography and include an allergic reaction to the dye, kidney failure, formation of a clot around the catheter that then blocks the artery, hemorrhaging due to puncturing of the artery by the catheter, and stroke induced by arterial blockage by debris knocked off the wall of the artery by the catheter. This procedure carries a 1.3% percent risk of transient neurological complication, and a 0.1% risk (1 in 1,000) of creating permanent stroke damage. Similar to coronary angiography, this procedure is highly risky, is only used when absolutely necessary, and cannot be prescribed for general screening of the population.

A non-invasive method of cerebral arteriography utilizing intravenous injection of the subject nanoparticle contrast agent may now be administered on a routine basis or to members of at-risk groups. Such a course of treatment should provide a major advance in the management of stroke by curtailing many sudden and unexpected strokes, and the subsequent incapacitation or death.

Renal artery stenosis greater than or equal to 50% is seen in approximately 20% of patients aged 65 years or older. Significant renal artery stenosis is defined as either a cross sectional narrowing of the artery greater than or equal to 60%, or any narrowing with a measured intra-arterial blood pressure difference greater than 5 mm of mercury. Current renal angiography requires puncturing an artery and snaking a catheter to the kidneys before releasing the contrast agent.

The severe risks involved in this highly invasive procedure may be avoided by intravenous injection of the subject nanoparticle contrast agent. As discussed above, metal nanoparticles having a size of 0.5 to 3 nm clear the blood rapidly after intravenous injection through the kidneys, being excreted in the urine. Consequently, the metal nanoparticles become concentrated in this exit pathway. This makes them an excellent choice for assaying renal function and visualizing the process to aid in diagnosing kidney conditions. The imaging procedure may be delayed for a period after injection of the contrast agent to ensure that the contrast agent has sufficiently concentrated in the kidneys. Alternatively, the images may be taken over a longer period of time to optimally record these events.

There are many other medical conditions where it would be of value to assess the blood flow to various regions or organs, such as with diabetes, especially to prevent amputations, and to detect embolisms and life-threatening throbophlebitis. For example, after intravenous injection, the contrast agent goes through the venous system back to the vena cava, then the right side of the heart, then to the lungs, then to the left side of the heart, then to the aorta and body arteries. It takes about ten seconds for the contrast agent to reach the brain. By analyzing the time course of the signal, the blood flow can be determined. Blood flow provides an accurate assessment of heart function, and is also an important overall measure of tissue function and the health, diseased tissue commonly showing a reduction in blood flow. Intravenous injection of a suitable amount of a non-targeted nanoparticle contrast agent in accordance with the invention provides a general vascular contrast agent that may be used to detect such medical conditions.

Angiograms are also useful for assessing abdominal aneurism, deep venous thromboses, pulmonary function, renal transplant function, portal vein and mesenteric artery imaging to evaluate disorders of the abdomen, pulmonary shunts and venous anomalies. Procedures in accordance with the invention may also be performed to see if the aorta is blocked, narrowed, leaking, or misshapen. Abdominal angiograms are currently obtained by injecting a radio-opaque dye into the aorta. As with other trans-arterial procedures, this is concomitant with significant risks. Risk from the dyes used include anaphylactic shock and possible death, unconsciousness, injury to the kidneys, formation of a blood clot around the catheter that may block the artery, the catheter may puncture the artery, making it bleed, or dislodging some debris off the wall of the artery, causing blockage elsewhere in the artery, possibly causing a stroke or heart attack, and surgery may be needed to attempt to correct some of these complications. Improved angiographic contrast agents of the type disclosed herein give comparable images by trans-venous (intravenous) administration.

Using the contrast agents of this invention, intravenous injection produces high contrast in all vessels in the heart, as well the atria and ventricles. This additional data may be used to computationally correct for motion of the heart before combining data sets for reconstruction. Intuitively, the contrast of the atria, ventricles, and other vessels provides for each image clear and distinct information about the part of the heartbeat that is captured by that image, as well as slight differences between ECG-gated data. Furthermore, by cross-correlation and mapping or morphing techniques, the data sets can be corrected for displacements. Data can then be combined to produce an accurate tomogram with the required resolution to visualize partial senses in coronary arteries with certainty. This overcomes the current limitation with existing x-ray equipment and algorithms in producing accurate morphology to 0.25 mm resolution in 2 mm coronary arteries in the beating heart.

After intravenous injection, the blood flows to one side of the heart, the lungs, the other side of the heart, then to the arteries. Consequently, the use of time lapse imaging after an intravenous injection allows isolation of these circulation segments by taking time lapse or properly timed images. It should be stressed, however, that computed tomography allows one to see internal detail from the three dimensional reconstruction, and structures (such as the coronary arteries) are not obscured from view as they might be on simple planar x-rays if contrast is also in surrounding tissues.

Targeted contrast agents utilizing antibodies as the targeting moiety may be administered intra-peritoneally, since the antibodies find their way quite efficiently into the bloodstream. For imaging target sites, an optimum combination of target site contrast agent concentration and target site to background contrast agent distribution is desired. Typically, these optimum combinations occur some period of time after intravenous injection of the contrast agent, with the time interval being dependent on the specific targeting moiety that is used. For example, anti-tumor antibodies typically reach a peak tumor to non-tumor distribution ratio after about 22 hours after injection. However there is some washout of the contrast agent from the tumor over this time period, so the amount concentrated at the tumor is typically less than at earlier times. For imaging, antibody fragments (such as Fab, which is ⅓ the size of an IgG antibody) are preferred since they diffuse quicker and better into tumors, achieving the best conditions of tumor-to-background and tumor uptake in approximately one hour. Pharmacokinetic studies need to be performed to determine the optimal time for imaging each targeting moiety. For vascular non-targeted imaging, the best image is usually achieved shortly after injection, before the blood level clears.

The above-discussed methods focus predominantly on use of non-radioactive elements that absorb x-rays to produce enhanced contrast. Use of radioactive isotopes of the metal or shell atoms in the nanoparticles however, permits imaging by gamma imaging devices, single photon emission computed tomography (SPECT), or other radioactive detectors. There are particular instances where this is of advantage, since radioactive detection is extremely sensitive, and fewer labeled target molecules need be detected, i.e., lower concentrations of target-seeking compounds may be imaged.

The imaging agents of this invention and methods also include detection by other means than use of x-ray absorption. X-rays impinging on these agents cause secondary electrons to be emitted as well as fluorescent photons, and the primary beam is scattered off-axis and can be reduced in energy, as well as causing further events and emissions in the target materials. Many of these events can be measured by various detectors, instruments, and spectrophotometers. Thus, imaging or simple detection, which does not require an image, but merely identifies the presence or amount of the agent, may be achieved by such other detection and imaging devices.

In addition to x-rays, other forms of electromagnetic probes may be employed to detect or image the agents. This includes, but is not limited to, the use of: static magnetic fields, visible light, lasers, ultrasound, infrared, microwave, radio frequencies, magnetic resonance (radio-frequency waves), ultraviolet radiation, and other electromagnetic radiation at various frequencies. Various other sources may be employed, including, but not limited to: electrons, protons, ion beams, and neutrons. Many of these sources produce secondary effects that can be measured, for example, specific heating caused by energy absorption of the sample, which can then be detected or imaged. Ones skilled in the art will be familiar with the use of sources other than x-rays to produce detection or imaging of metal particles.

EXAMPLE 1

Gold nanoparticles having a diameter of approximately 1.8 nm were injected intravenously into the tail veins of mice to produce a blood concentration of up to 10 mg Au/ml. All mice showed normal weight gain with no observable side effects. Necropsy was done after two weeks and organs appeared normal. Blood was taken to assay hematology and clinical chemistry values. The results of such tests are provided in Table 3.

reach an equilibrium blood concentration of 10 mg Au/ml. Mice were anesthetized and x-ray images recorded on film using 35 kVp x-rays. Images revealed excellent contrast of major vasculature including the femoral arteries, the branching pattern of vessels supplying the kidney, lungs, and intestine, as well as vessels in the front legs and neck. Upon magnified viewing, vessels at least as small as 0.1 mm could be clearly seen.

EXAMPLE 3

Healthy mice were injected intravenously with varying sizes of gold nanoparticles, including those with 1.4, 1.8, 2.0, 3, 10, 40, and 100 nm diameters. No acute toxicity was observed.

EXAMPLE 4

Gold nanoparticles were covalently attached to Fab' antibody fragments and were shown to target antigen on blots. 100 ng mouse IgG was spotted onto nitrocellulose, and buffer only spotted as a control. After drying, membranes were blocked with 4% bovine serum albumin, washed, then incubated with gold nanoparticles that had goat anti-mouse Fab' attached. After washing, blots were developed with silver enhancer. A dense spot only appeared at the target antigen location, indicating specific immunotargeting of gold particles.

It should be appreciated that a number of unique applications are enabled by the above described discoveries. For example, by intravenous administration of the agents of this invention, blood vessels of the heart, brain, kidney, and other organs may be imaged at high resolution with minimal risk to the patient. By targeting the agents either by their size or by combining the metal particle with a molecule that binds to a desired target, contrast of specific sites, such as tumors

TABLE 3

Blood levels in mice two weeks after gold particle injection

| Gold initial blood con (mg/ml) | Hgb (g/dl) | HCT | GLUCm (mg/dl) | CREm (mg/dl)- creatinine | BUNm (mg/dl) | TPm (g/dl)- total protein | ALBm (g/dl) | PHOSm (mg/dl) | TBIL (mg/dl) | DBILm (mg/dl) | GGT (IU/L) | AST (IU/L) | ALT (IU/L) | ALP (IU/L) |
|---|---|---|---|---|---|---|---|---|---|---|---|---|---|---|
| 10 | 13.8 | 40.0 | 213.0 | 0.3 | 25.0 | 4.1 | 1.3 | 7.9 | 0.4 | 0.1 | <5 | 67.0 | 27.0 | 50.0 |
| 10 | nd | nd | 272.0 | 0.3 | 22.0 | 4.2 | 1.4 | 6.8 | 0.3 | 0.1 | <5 | 95.0 | 32.0 | 55.0 |
| 5 | 14.6 | 42.5 | 276.0 | 0.3 | 22.0 | 4.4 | 1.5 | 7.6 | 0.0 | 0.1 | <5 | 62.0 | 28.0 | 48.0 |
| 5 | 14.1 | 41.3 | 238.0 | 0.2 | 24.0 | 4.0 | 1.4 | 7.7 | 0.1 | 0.1 | <5 | 64.0 | 25.0 | 48.0 |
| 0 (Control) | 14.7 | 42.2 | 253.0 | 0.3 | 20.0 | 3.9 | 1.3 | 7.3 | 0.3 | 0.1 | <5 | 54.0 | 23.0 | 51.0 |
| 0 (Control) | 15.3 | 44.1 | 251.0 | 0.3 | 24.0 | 4.3 | 1.4 | 6.3 | 0.2 | 0.1 | <5 | 71.0 | 25.0 | 59.0 |
| 0 (Control) | 13.4 | 38.3 | 227.0 | 0.3 | 28.0 | 4.1 | 1.4 | 6.1 | 0.1 | 0.1 | <5 | 80.0 | 22.0 | 50.0 |
| 0 (Control) | 13.8 | 40.0 | 266.0 | 0.2 | 20.0 | 3.8 | 1.3 | 6.6 | 0.2 | 0.1 | <5 | 81.0 | 24.0 | 46.0 |
| normal mouse | 10.2 −16.5 | 39 −169 | NA | 0.2 −0.9 | 8 −32 | 3.5 −7.2 | 2.5 −3.0 | 5.7 −9.2 | 0.0 −0.9 | NA | NA | 54 −298 | 17 −77 | 35 −96 | nd—not done due to lack of blood volume

NA—not available normal values from http://www.ahc.umn.edu/rar/refvalues.html

This study showed all values were within the normal range. This indicates that, to the extent of such testing, the gold nanoparticles are safe and non-toxic at a dose of 10 mg Au/ml blood concentration.

EXAMPLE 2

Gold nanoparticles having a diameter of approximately 2 nm were injected into mice intravenously via the tail vein to or blood clots, may be achieved. Contrasting agents in accordance with the invention may be used to assess abdominal function, kidney function, coronary function, strokes and brain function. Similarly, such agents may be used to enhance bone imaging, localize sites of infection, and to detect atherosclerotic plaques. It should also be appreciated that the agents and methods disclosed herein are non-toxic at levels required for effective use, provide images having resolutions which are generally substantially greater than those provided by conventional agents and techniques, extend imaging to one hour or more, allow detection of tumors that would be missed by other techniques, and enable widespread medical screening which is currently precluded due to the risk and expense of existing procedures. It should further be appreciated that the subject media and methods will enable prophylactic life-style change (i.e., in diet, exercise, work) and/or drug therapy to be initiated in a timely manner so as to reduce the likelihood of, or prevent heart attacks in individuals so identified as being at high risk for them, safely, rapidly, and economically. It is expected that such screening would cost no more than does the periodic colonoscopic screening presently recommended for Americans over age 50 to avert colon cancer.

Although the description contains many examples and specifics, these should not be construed as limiting the scope of the invention, but as merely providing illustrations of some of the presently preferred embodiments.

What is claimed is:

1. A method for delivering a radiographic contrast agent to a targeted portion of a body of a living animal, the method comprising the steps of:

intravenously administering a quantity of nanoparticles into the body of the living animal, each of the nanoparticles having a metallic core, substantially each of the nanoparticles also having a surface layer composed of a material surrounding the metallic core, the material of the surface layer including an organothiol and a component having an affinity for the targeted portion of the body, a sufficient quantity of the nanoparticles being administered to contrast the targeted portion of the body under irradiation; and irradiating the targeted portion of the body with penetrating radiation.

2. The method of claim 1 wherein each metal nanoparticle has a core composed of a material selected from gold, platinum, palladium, thallium, bismuth, osmium, iridium, silver, tungsten, lead, tantalum, and uranium.

3. The method of claim 1 wherein the component of the material of the surface layer is selected from an antibody, an antibody fragment, a peptide, a lipid, a carbohydrate, a nucleic acid, and a drug.

4. The method of claim 1 wherein the surface layer is coupled directly to the core by a sulfur atom.

5. The method of claim 1 wherein substantially each of the nanoparticles also has an organic inner shell disposed intermediate the metallic core and the surface layer, the surface layer being covalently coupled to the inner shell.

6. The method of claim 1 wherein the surface layer is adsorbed non-covalently to the metallic core.

7. The method of claim 1 wherein substantially each of the nanoparticles also has an organic inner shell disposed intermediate the metallic core and the surface layer, the surface layer being adsorbed non-covalently to the inner shell.

8. The method of claim 1 wherein the targeted portion of the body is cancerous cells, the component of the material of the surface layer being selected from antibodies, antibody fragments, and peptides.

9. The method of claim 1 wherein the targeted portion of the body is a blood clot, the component of the material of the surface layer being selected from anti-fibrin, anti-D-dimer antibodies, and peptides.

10. The method of claim 1 further comprising step of preparing the nanoparucles by:

extracting blood from the animal;

isolating leukocytes or white blood cells from the extracted blood; and labeling the isolated leukocytes or white blood cells with nanoparticles;

wherein the nanoparticles are attracted to an infection site.

11. The method of claim 1 wherein the targeted portion of the body is an atherosclerotic plaque, the component of the material of the surface layer being a peptide that binds to activated platelets.

12. The method of claim 1 wherein the targeted portion of the body is an atherosclerotic plaque, the component of the material of the surface layer being a lipophilic group.

13. The method of claim 12 wherein the lipophilic group is selected from fatty acids, phospholipids, and cholesterol.

14. The method of claim 1 wherein the targeted portion of the body is irradiated a predetermined period of time after the nanoparticles are administered, whereby an optimum combination of targeted portion nanoparticle concentration and targeted portion to background nanopartiacle distribution is achieved.

15. The method of claim 1 wherein the material of the surface layer also includes a component that absorbs X-rays.

16. The method of claim 1 wherein the material of the surface layer also includes a radioactive isotope.

17. The method of claim 1 wherein the metallic core includes a radioactive isotope.

18. A method for delivering a radiographic contrast agent to a targeted portion of a body of a living animal, the method comprising the steps of:

intravenously administering a quantity of nanoparticles into the body of the living animal, each of the nanoparticles having a core composed of a material selected from gold, platinum, palladium, thallium, bismuth, osmium, iridium, silver, tungsten, lead, tantalum, and uranium, the core having a size of 1.8 to 3 nm, substantially each of the nanoparticles also having a surface layer composed of a material surrounding the metallic core, the material of the surface layer including a component having an affinity for the targeted portion of the body, the component of the material of the surface layer being selected from an antibody, an antibody fragment, a peptide, a lipid, a carbohydrate, a nucleic acid, and a drug, a sufficient quantity of the nanoparticles being administered to contrast the targeted portion of the body under irradiation; and irradiating the targeted portion of the body with penetrating radiation.

19. The method of claim 18 wherein substantially each of the nanoparticles also has an organic inner shell disposed intermediate the core and the surface layer.

20. The method of claim 18 wherein the targeted portion of the body is irradiated a predetermined period of time after the nanoparticles are administered, whereby an optimum combination of targeted portion nanoparticle concentration and targeted portion to background nanpartiacle distribution is achieved.

* * * * *

UNITED STATES PATENT AND TRADEMARK OFFICE
CERTIFICATE OF CORRECTION

PATENT NO. : 6,818,199 B1
DATED : November 16, 2004
INVENTOR(S) : Hainfeld

It is certified that error appears in the above-identified patent and that said Letters Patent is hereby corrected as shown below:

Column 21,
Line 61, delete "nanoparucles" and insert -- nanoparticles --.

Signed and Sealed this

Seventh Day of February, 2006

JON W. DUDAS
*Director of the United States Patent and Trademark Office*